US009579632B2

(12) United States Patent
Dakka et al.

(10) Patent No.: US 9,579,632 B2
(45) Date of Patent: Feb. 28, 2017

(54) DEHYDROGENATION CATALYST AND PROCESS

(75) Inventors: Jihad M. Dakka, Whitehouse Station, NJ (US); Lorenzo C. DeCaul, Langhorne, PA (US); Terry E. Helton, Bethlehem, PA (US); Keith H. Kuechler, Friendswood, TX (US); Jenna L. Wallace, Bethlehem, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 177 days.

(21) Appl. No.: 13/990,440

(22) PCT Filed: Dec. 2, 2011

(86) PCT No.: PCT/US2011/063110
§ 371 (c)(1),
(2), (4) Date: Aug. 16, 2013

(87) PCT Pub. No.: WO2012/082407
PCT Pub. Date: Jun. 21, 2012

(65) Prior Publication Data
US 2014/0066663 A1 Mar. 6, 2014

Related U.S. Application Data

(60) Provisional application No. 61/424,242, filed on Dec. 17, 2010.

(30) Foreign Application Priority Data

Mar. 15, 2011 (EP) .................... 11158168

(51) Int. Cl.
*B01J 23/62* (2006.01)
*B01J 35/00* (2006.01)
*B01J 37/02* (2006.01)
*C07C 37/06* (2006.01)
*C07C 37/07* (2006.01)
*B01J 21/08* (2006.01)
*B01J 23/24* (2006.01)
*B01J 23/32* (2006.01)

(52) U.S. Cl.
CPC ......... *B01J 23/626* (2013.01); *B01J 35/0066* (2013.01); *B01J 37/0207* (2013.01); *C07C 37/06* (2013.01); *C07C 37/07* (2013.01); *B01J 21/08* (2013.01); *B01J 23/24* (2013.01); *B01J 23/32* (2013.01)

(58) Field of Classification Search
CPC .. B01J 23/626; B01J 35/0066; B01J 37/0207; B01J 21/08; B01J 23/24; B01J 23/32; C07C 37/06; C07C 37/07
See application file for complete search history.

(56) References Cited

U.S. PATENT DOCUMENTS

| 2,620,314 | A | * | 12/1952 | Hoekstra | ............................ 502/8 |
| 3,354,078 | A | | 11/1967 | Miale et al. | |
| 3,358,044 | A | | 12/1967 | Russell et al. | |
| 3,514,492 | A | | 5/1970 | Juguin et al. | |
| 3,519,575 | A | | 7/1970 | Bozik et al. | |
| 3,534,110 | A | | 10/1970 | Fuller | |
| 3,534,116 | A | | 10/1970 | Fuller | |
| 3,580,970 | A | | 5/1971 | Swift | |
| 3,691,102 | A | | 9/1972 | Swift | |
| 3,864,284 | A | | 2/1975 | Clippinger et al. | |
| 3,909,451 | A | * | 9/1975 | Wilhelm | ....................... 502/226 |
| 4,008,180 | A | * | 2/1977 | Rausch | ......................... 502/223 |
| 4,048,245 | A | | 9/1977 | Pollitzer et al. | |
| 4,094,918 | A | | 6/1978 | Murtha et al. | |
| 4,122,125 | A | | 10/1978 | Murtha et al. | |
| 4,130,597 | A | | 12/1978 | Wilhelm | |
| 4,133,839 | A | | 1/1979 | Hayes | |
| 4,177,165 | A | | 12/1979 | Murtha et al. | |
| 4,206,082 | A | | 6/1980 | Murtha et al. | |
| 4,417,076 | A | | 11/1983 | Rozovsky et al. | |
| 4,439,409 | A | | 3/1984 | Puppe et al. | |
| 4,542,248 | A | * | 9/1985 | Lucien | ................... B01J 23/626 585/315 |
| 4,826,667 | A | | 5/1989 | Zones et al. | |
| 4,870,217 | A | | 9/1989 | Knifton | |
| 4,929,762 | A | | 5/1990 | Matsunaga et al. | |
| 4,933,507 | A | | 6/1990 | Inoki et al. | |

(Continued)

FOREIGN PATENT DOCUMENTS

| CN | 1829676 | 9/2006 |
| EP | 0 293 032 | 11/1988 |

(Continued)

OTHER PUBLICATIONS

Miale, "*Catalysis by Crystalline Aluminosilicates—IV. Attainable Catalytic Cracking Rate Constants, and Superactivity*", Journal of Catalysis, vol. 6, pp. 278-287, 1966.
Weisz, "*Superactive Crystalline Aluminosilicate Hydrocarbon Catalysts*", Journal of Catalysis, vol. 4, pp. 527-529, 1965.
Olson et al., "*Chemical and Physical Properties of the ZSM-5 Substitutional Series*", Journal of Catalysis, vol. 61, pp. 390-396, 1980.
Savostin et al., "The Addition of Tin to Platinum Alumina Catalysts", Order of Labor's Red Banner Institute of Catalysis, Siberian Dept., Academy of Sciences of the USSR, 1979, No. 1, pp. 18-21. (translation).

*Primary Examiner* — Paul A Zucker
*Assistant Examiner* — Mark Luderer
(74) *Attorney, Agent, or Firm* — Stephen A. Baehl

(57) ABSTRACT

A catalyst composition comprises (i) a support; (ii) a dehydrogenation component comprising at least one metal or compound thereof selected from Groups 6 to 10 of the Periodic Table of Elements; and (iii) tin or a tin compound, wherein the tin is present in an amount of 0.01 wt % to about 0.25 wt %, the wt % based upon the total weight of the catalyst composition.

4 Claims, 11 Drawing Sheets

(56) References Cited

U.S. PATENT DOCUMENTS

| | | | |
|---|---|---|---|
| 4,954,325 | A | 9/1990 | Rubin et al. |
| 5,053,571 | A | 10/1991 | Makkee |
| 5,236,575 | A | 8/1993 | Bennett et al. |
| 5,250,277 | A | 10/1993 | Kresge et al. |
| 5,256,348 | A | 10/1993 | Waller |
| 5,362,697 | A | 11/1994 | Fung et al. |
| 6,037,513 | A | 3/2000 | Chang et al. |
| 6,049,018 | A | 4/2000 | Calabro et al. |
| 6,077,498 | A | 6/2000 | Diaz Cabañas et al. |
| 6,187,984 | B1 * | 2/2001 | Wu ................ B01J 23/626 585/654 |
| 6,201,157 | B1 | 3/2001 | Keenan |
| 6,720,462 | B2 | 4/2004 | Kuhnle et al. |
| 6,730,625 | B1 | 5/2004 | Chang et al. |
| 6,756,030 | B1 | 6/2004 | Rohde et al. |
| 7,579,511 | B1 | 8/2009 | Dakka et al. |
| 2007/0032681 | A1 | 2/2007 | Walsdorff et al. |
| 2008/0051618 | A1 * | 2/2008 | Kim et al. ................ 585/431 |
| 2008/0262281 | A1 | 10/2008 | Walsdorff et al. |
| 2011/0021844 | A1 | 1/2011 | Dakka et al. |
| 2011/0105805 | A1 | 5/2011 | Buchanan et al. |
| 2014/0323782 | A1 | 10/2014 | Chen et al. |

FOREIGN PATENT DOCUMENTS

| | | |
|---|---|---|
| JP | H02-188542 | 7/1990 |
| JP | 2637812 B2 | 8/1997 |
| JP | 2004-196638 | 7/2004 |
| WO | WO91/06616 | 5/1991 |
| WO | WO 97/17290 | 5/1997 |
| WO | WO 2005/009937 | 2/2005 |
| WO | WO2006/078240 | 7/2006 |
| WO | WO 2007/084440 | 7/2007 |
| WO | WO 2009/025939 | 2/2009 |
| WO | WO 2009/128984 | 10/2009 |
| WO | WO 2009/131769 | 10/2009 |
| WO | WO 2010/024975 | 3/2010 |
| WO | WO2010/024975 * | 3/2010 |
| WO | WO 2011/096989 | 8/2011 |
| WO | WO 2011/096990 | 8/2011 |
| WO | WO 2011/096992 | 8/2011 |
| WO | WO 2011/096993 | 8/2011 |
| WO | WO 2011/096997 | 8/2011 |
| WO | WO 2011/096998 | 8/2011 |
| WO | WO 2011/096999 | 8/2011 |
| WO | WO 2011/162850 | 12/2011 |
| WO | WO 2012/050665 | 4/2012 |

* cited by examiner

DEHYDROGENATION CATALYST AND PROCESS

PRIORITY CLAIM

This application is a National Stage Application of International Application No. PCT/US2011/063110 filed Dec. 2, 2011, which claims priority to U.S. Provisional Application Ser. No. 61/424,242 filed Dec. 17, 2010, and European Application No. 11158168.2 filed Mar. 15, 2011, which are incorporated herein by reference in their entirety.

CROSS REFERENCE TO RELATED APPLICATIONS

This application is related to U.S. Publication Nos. 2011-0021844 published Jan. 27, 2011; 2011-0105805 published May 5, 2011; International Patent Cooperation Treaty Publication Nos. WO2011/096993; WO2011/096997; WO2011/096992; WO2011/096999; WO2011/096990; WO2011/096989, all published Aug. 11, 2011; International Patent Cooperation Treaty Application Nos. PCT/US2011/031055 filed Apr. 4, 2011; PCT/US2011/049130 filed Aug. 25, 2011; and U.S. Provisional Application Ser. No. 61/468,298 filed Mar. 28, 2011.

FIELD

The present invention relates to a dehydrogenation catalyst, its synthesis and its use in the dehydrogenation of cycloaliphatic alcohols and ketones to the corresponding hydroxyaromatic alcohols and, in particular, in the dehydrogenation of cyclohexanone to produce phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, due to a developing shortage, the cost of propylene is likely to increase. Thus, a process that uses higher alkenes instead of propylene as feed and co-produces higher ketones, rather than acetone, may be an attractive alternative route to the production of phenols.

One such process involves the hydroalkylation of benzene to produce cyclohexylbenzene, followed by the oxidation of the cyclohexylbenzene (analogous to cumene oxidation) to cyclohexylbenzene hydroperoxide, which is then cleaved to produce phenol and cyclohexanone in substantially equimolar amounts. Such a process is described in, for example, U.S. Pat. No. 6,037,513.

However, one problem in producing phenol by way of the cleavage of cyclohexylbenzene hydroperoxide is that the cyclohexanone and phenol produce an azeotropic mixture composed of 28 wt % cyclohexanone and 72 wt % phenol. Thus any attempt to separate the cleavage effluent by simple distillation results in this azeotropic mixture. To obviate this problem it has been proposed to integrate the cyclohexylbenzene oxidation and cleavage process with a dehydrogenation step whereby at least part of the cyclohexanone is converted to additional phenol (see International Patent Publication No. WO2010/024975). Such a dehydrogenation step is generally achieved by contacting the cyclohexanone with a supported noble metal catalyst at a temperature of about 250° C. to about 500° C.

For example, U.S. Pat. No. 3,534,110 discloses a process for the catalytic dehydrogenation of cyclohexanone and/or cyclohexanol to phenol over a catalyst comprising platinum and preferably iridium on a silica support. The catalyst also contains 0.5 wt % to 3 wt % of an alkali or alkaline earth metal compound, which, according to column 3, lines 43 to 49, should be incorporated after addition of the platinum since otherwise the resulting catalyst composition has inferior activity, selectivity, and life.

In addition, U.S. Pat. No. 3,580,970 discloses a process for the dehydrogenation of cycloaliphatic alcohols and ketones to the corresponding hydroxyaromatic alcohols in the presence of a catalyst comprising a Group VIII metal, particularly nickel, and tin in a molar amount of about 1.7 to about 15 moles of Group VIII metal per mole of tin. The catalyst may further comprise a silica support and an alkali metal stabilizing agent. In the Examples, the catalyst contains between 2.22 wt % and 14.2 wt % tin.

U.S. Pat. No. 4,933,507 discloses that phenol can be produced by dehydrogenating cyclohexenone through a vapor-phase reaction in the presence hydrogen using a solid-phase catalyst having platinum and alkali metal carried on a support, such as silica, silica-alumina or alumina. The catalyst is prepared by first treating the support with an aqueous solution of chloroplatinic acid, etc. to have platinum chloride carried on the support, and then treating the support to have an alkali metal compound such as $K_2CO_3$ supported thereon, and finally reducing the so treated support. The content of alkali metal in the catalyst is preferably in the range of 0.5 wt %-2.0 wt % in terms of $Na_2O$ based on the weight of the support and in the range of 0.2 wt %-3.0 wt % in terms of $K_2CO_3$ based on the weight of the platinum.

U.S. Pat. No. 7,285,685 discloses a process for the dehydrogenation of a saturated carbonyl compound, such as cyclohexanone, in the gas phase over a heterogeneous dehydrogenation catalyst comprising platinum and/or palladium and tin on an oxidic support, such as zirconium dioxide and/or silicon dioxide ($SiO_2$). In general, the dehydrogenation catalyst contains from 0.01 wt % to 2 wt %, preferably from 0.1 wt % to 1 wt %, particularly preferably from 0.2 wt % to 0.6 wt %, of palladium and/or platinum and from 0.01 wt % to 10 wt %, preferably from 0.2 wt % to 2 wt %, particularly preferably from 0.4 wt % to 1 wt %, based on the total weight of the dehydrogenation catalyst. In addition, the dehydrogenation catalyst can further comprise one or more elements of Groups I and/or II, preferably potassium and/or cesium, which are added to the catalyst as aqueous solutions of compounds which can be converted into the corresponding oxides by calcination. In the only catalyst preparation Example, an aqueous solution containing $CsNO_3$ and $KNO_3$ is added to a silica/titania support after the support has been impregnated with a solution of $SnCl_2 \cdot 2H_2O$ and $H_2PtCl_6 \cdot 6H_2O$ in ethanol, then dried at 100° C. for 15 hours and calcined at 560° C. for 3 hours.

One problem with existing cyclohexanone dehydrogenation catalysts is that they also tend to catalyze the competing hydrogenolysis of cyclohexanone to produce pentane, pentene and carbon monoxide. This not only leads to loss of valuable cyclohexanone, but also the pentene can react with benzene normally present in the cyclohexanone feed to produce pentylbenzene which is difficult to separate from the phenol product. In addition, any carbon monoxide produced passes into the co-produced hydrogen stream so that the hydrogen stream requires additional processing to reduce the CO to very low levels before the hydrogen can be recycled to, for example, the original benzene hydroalkylation step.

There is therefore a need for a cyclohexanone dehydrogenation catalyst having improved selectivity to the production of phenol and reduced selectivity to side reactions, such as hydrogenolysis to pentane, pentene and carbon monoxide.

According to the present invention, it has now been found that the addition of small amounts of tin to a supported, Group 6 to 10 metal-containing cyclohexanone dehydrogenation catalyst reduces the formation of pentylbenzene and carbon monoxide as well as improves the stability of the catalyst. Preferably, the tin is incorporated in the catalyst before the Group 6 to 10 metal.

SUMMARY

In one aspect, the invention resides in a catalyst composition comprising (i) a support; (ii) a dehydrogenation component comprising at least one metal or compound thereof selected from Groups 6 to 10 of the Periodic Table of Elements; and (iii) tin or a tin compound, wherein the tin is present in an amount of about 0.01 wt % to about 0.25 wt %, the wt % based upon the total weight of the catalyst composition.

Conveniently, the tin is present in an amount of about 0.05 wt % to about 0.25 wt %, such as about 0.05 wt % to about 0.15 wt %, of tin based upon the total weight of the catalyst composition.

Conveniently, the support is selected from the group consisting of silica, a silicate, an aluminosilicate, zirconia, and carbon nanotubes, and preferably comprises silica.

Conveniently, the dehydrogenation component is selected from platinum, palladium and compounds and mixtures thereof, and preferably comprises platinum.

Generally, the dehydrogenation component is present in an amount of about 0.01 wt % to about 2 wt %, about 0.5 wt % to about 1.5 wt %, upon the total weight of the catalyst composition.

In a further aspect, the invention resides in a method for preparing a catalyst composition, the method comprising:
(a) treating a support with tin or a compound thereof;
(b) heating the treated support at a temperature of about 100° C. to about 700° C.; and
(c) impregnating the support with a dehydrogenation component comprising at least one metal or compound thereof selected from Groups 6 to 10 of the Periodic Table of Elements,
wherein the impregnating (c) is effected after or at the same time as the treating (a).

Conveniently, said heating (b) is conducted in an oxygen-containing atmosphere.

In one embodiment, said impregnating (c) is effected after the treating (a) and the heating (b) and the method further comprises:
(d) heating the impregnated support at a temperature of about 100° C. to about 700° C.

Conveniently, said heating (d) is conducted in an oxygen-containing atmosphere, generally at a temperature of about 200° C. to about 500° C., such as about 300° C. to about 450° C., for a time of about 1 to about 10 hours.

In yet a further aspect, the invention resides in a process for the dehydrogenation of a cycloaliphatic alcohol or ketone to the corresponding aromatic alcohol, the process comprising contacting a feed comprising a cycloaliphatic alcohol or ketone under dehydrogenation conditions with catalyst composition comprising (i) a support; (ii) a dehydrogenation component comprising at least one metal or compound thereof selected from Groups 6 to 10 of the Periodic Table of Elements; and (iii) tin or a tin compound present in an amount of about 0.01 wt % to about 0.25 wt % of tin based upon the total weight of the catalyst composition.

In one embodiment, said feed comprises cyclohexanone.

Conveniently, said dehydrogenation conditions comprise a temperature of about 250° C. to about 500° C., a pressure of about 100 kPa to about 3550 kPa, a weight hourly space velocity of about 0.2 $hr^{-1}$ to 50 $hr^{-1}$, and a hydrogen to cyclohexanone-containing feed molar ratio of about 2 to about 20.

DETAILED DESCRIPTION

Figure 1:
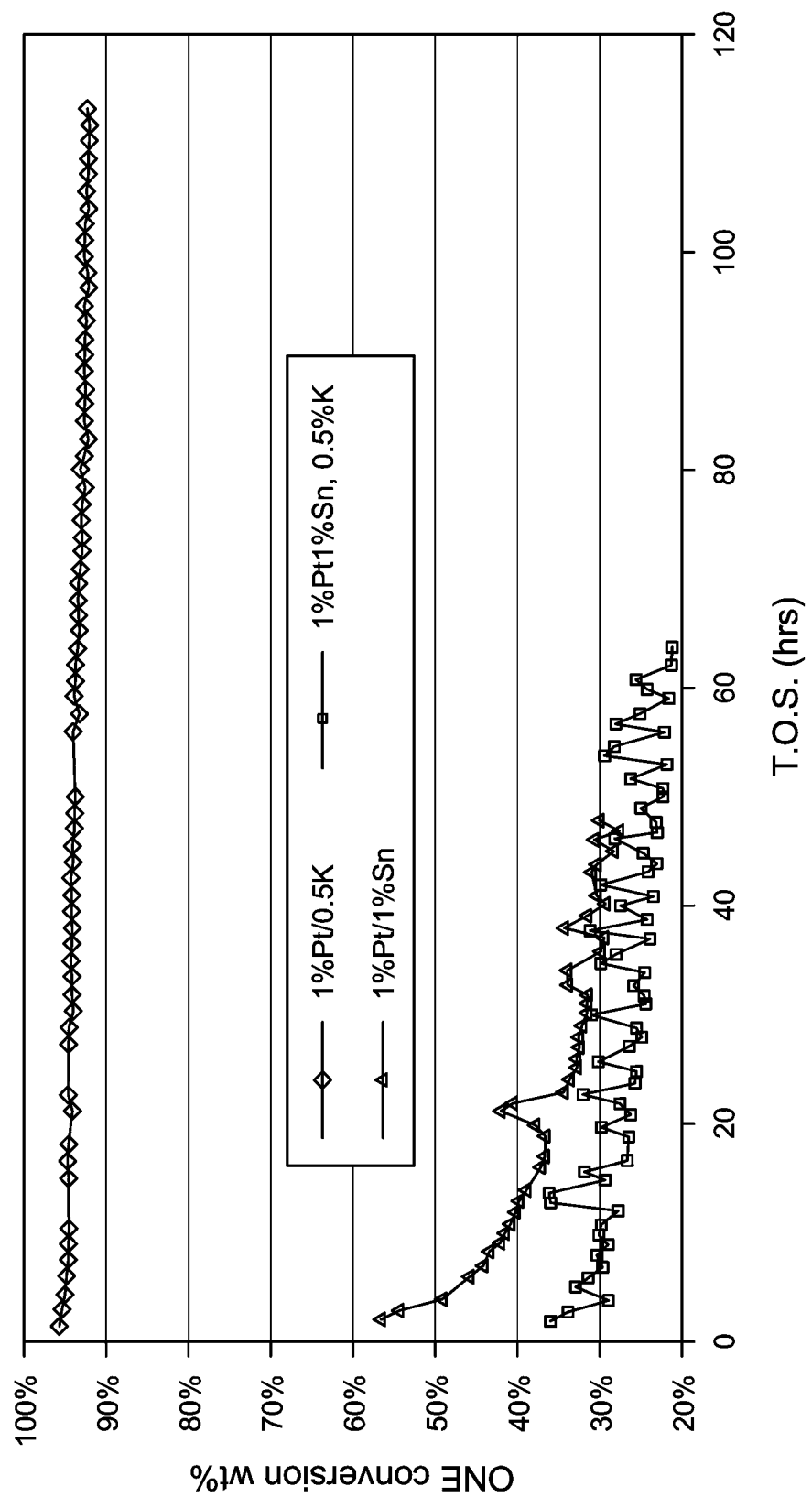
FIG. 1 is a graph comparing cyclohexanone conversion against time on stream for the 1% Pt/1% Sn/$SiO_2$ catalyst of Example 7 and the 1% Pt/1% Sn/0.5% K/$SiO_2$ catalyst of Example 9B with that of the 1% Pt/0.5% K/$SiO_2$ catalyst of Comparative Example 1.

Described herein is a catalyst composition and a method of its synthesis, in which the catalyst composition comprises (i) a support; (ii) a dehydrogenation component comprising at least one metal or compound thereof selected from Groups 6 to 10 of the Periodic Table of Elements; and (iii) tin or a tin compound present in an amount of about 0.01 wt % to about 0.25 wt % of tin based upon the total weight of the catalyst composition. The catalyst composition is useful in the dehydrogenation of cycloaliphatic alcohols and ketones to the corresponding hydroxyaromatic alcohols and, in particular, in the dehydrogenation of cyclohexanone to produce phenol.

In one preferred embodiment, the present catalyst is employed to dehydrogenate cyclohexanone produced as a by-product in an integrated process for producing phenol via cyclohexylbenzene. In this process, benzene is hydroalkylated to produce cyclohexylbenzene, which then undergoes oxidation and cleavage to produce phenol and cyclohexanone. The cyclohexanone is then dehydrogenated to produce additional phenol together with hydrogen which is desirably recycled to the benzene hydroalkylation step. The present catalyst will therefore now be more particularly with reference to this preferred embodiment, although it will be appreciated that the catalyst can be employed to dehydrogenate other cycloaliphatic alcohols and ketones to their corresponding hydroxyaromatic alcohols.

Production of Cyclohexylbenzene

In the integrated process for producing phenol and cyclohexanone from benzene, the benzene is initially converted to cyclohexylbenzene by any conventional technique, including alkylation of benzene with cyclohexene in the presence of an acid catalyst, such as zeolite beta or an MCM-22 family molecular sieve, or by oxidative coupling of benzene to make biphenyl followed by hydrogenation of the biphenyl. However, in practice, the cyclohexylbenzene is generally produced by contacting the benzene with hydrogen under hydroalkylation conditions in the presence of a hydroalkylation catalyst whereby the benzene undergoes the following reaction (1) to produce cyclohexylbenzene (CHB):

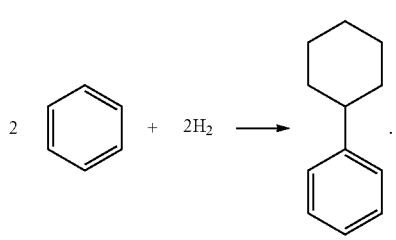
(1)

For an example of hydroalkylation of benzene in the presence of hydrogen for the production of cyclohexylbenzene, see U.S. Pat. Nos. 6,730,625 and 7,579,511 which are incorporated by reference. Also, see International Applications WO2009131769 or WO2009128984 directed to catalytic hydroalkylation of benzene in the presence of hydrogen for the production of cyclohexylbenzene.

Any commercially available benzene feed can be used in the hydroalkylation reaction, but preferably the benzene has a purity level of at least 99 wt %. Similarly, although the source of hydrogen is not critical, it is generally desirable that the hydrogen is at least 99 wt % pure.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa. Suitable values for the molar ratio of hydrogen to benzene are between about 0.15:1 and about 15:1, such as between about 0.4:1 and about 4:1 for example between about 0.4:1 and about 0.9:1.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes molecular sieves having the MWW framework topology. (Such crystal structures are discussed in the "Atlas of Zeolite Framework Types", Fifth edition, 2001, the entire content of which is incorporated as reference.)

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia, and silica-magnesia-zirconia.

Although the hydroalkylation reaction is highly selective towards cyclohexylbenzene, the effluent from the hydroalkylation reaction will normally contain some dialkylated products, as well as unreacted benzene and the desired monoalkylated species. The unreacted benzene is normally recovered by distillation and recycled to the alkylation reactor. The bottoms from the benzene distillation are further distilled to separate the monocyclohexylbenzene product from any dicyclohexylbenzene and other heavies. Depending on the amount of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, zeolite USY, and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 $hr^{-1}$ to about 10 $hr^{-1}$ on total feed, and a benzene/dicyclohexylbenzene weight ratio about of 1:1 to about 5:1.

One by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Typically, the hydrogenation-dehydrogenation component is present in an amount between about 0.1 wt % and about 10 wt % of the catalyst. A suitable inorganic promoter (c) comprises at least one metal or compound thereof selected from Group 1 of the Periodic Table of Elements, such as a tin compound. Typically, the promoter is present in an amount between about 0.1 wt % and about 5 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 $hr^{-1}$ to 50 $hr^{-1}$, and a hydrogen to hydrocarbon feed molar ratio of about 0 to about 20. As used herein, the numbering scheme for the Periodic Table Groups is as disclosed in Chemical and Engineering News, 63(5), 27 (1985).

The cyclohexylbenzene product from the hydroalkylation reaction can be fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent is subjected to a cleavage reaction to convert the cyclohexyl-1-phenyl-1-hydroperoxide to phenol and cyclohexanone. Cleavage may be conducted on oxidation reaction effluent, with or without the effluent undergoing any prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3 A molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Application No. WO 2009/025939.

Hydroperoxide Cleavage

The final reactive step in the conversion of the cyclohexylbenzene into phenol and cyclohexanone involves the acid-catalyzed cleavage of the cyclohexyl-1-phenyl-1-hydroperoxide produced in the oxidation step.

Generally, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm to no greater than 3000 wppm, or at least 150 wppm to and no greater than 2000 wppm of the acid catalyst, or at least 300 wppm and no greater than 1500 wppm of the acid catalyst, based upon total weight of the cleavage reaction mixture.

In one embodiment, the cleavage reaction mixture contains a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is acetone. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

Suitable cleavage conditions include a temperature of greater than 50° C. and no greater than 200° C., or at least 55° C. and no greater than 120° C., and a pressure of at least 1 psig and no greater than 370 psig (at least 7 kPa, gauge and no greater than 2,550 kPa, gauge), or at least 14.5 psig and no greater than 145 psig (at least 100 kPa, gauge and no greater than 1,000 kPa, gauge) such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major products of the cleavage reaction of cyclo-hexyl-1-phenyl-1-hydroperoxide are phenol and cyclohexanone, each of which generally comprise about 40 wt % to about 60 wt %, or about 45 wt % to about 55 wt % of the cleavage reaction product, such wt % based on the weight of the cleavage reaction product exclusive of unreacted cyclohexylbenzene and acid catalyst.

The cleavage reaction product also typically contains unreacted acid catalyst and hence at least a portion of the cleavage reaction product is normally neutralized with a basic material to remove or reduce the level of acid in the product.

Suitable basic materials include alkali metal hydroxides and oxides, alkali earth metal hydroxides and oxides, such as sodium hydroxide, potassium hydroxide, magnesium hydroxide, calcium hydroxide, calcium oxide, and barium hydroxide. Sodium and potassium carbonates may also be used, optionally at elevated temperatures.

In various embodiments, the basic material comprises one or more of: a caustic exchange resin (e.g., sulfonic ion-exchange resin); ammonia or ammonium hydroxide; a basic clay such as limestone, dolomite, magnesite, sepiolite, and olivine; an activated carbon and/or impregnated activated carbon; an anionic exchange resin, such as a weakly basic ion exchange resin having a styrene-divinyl benzene polymer backbone and an amine functional structure selected from —N(CH$_3$)$_2$, —NRH or —NR$_2$, where R is a hydrogen or an alkyl group containing 1 to 20 carbon atoms; an amine polysiloxane functionalized with ethylenediamine; an organic basic material grafted on microporous or mesoporous metal oxides; other organo-inorganic solids, such as zeolites exchanged with a metal selected from the group of lithium, sodium potassium, rubidium, cesium, calcium, barium, strontium, and radium; an oxide of Group III of the Periodic Table of Elements treated with a metal selected from lithium, potassium, sodium, rubidium, and cesium; a supported or solid alkali, alkaline-earth metal or organometallic; a magnesium silicate generally derived from the interaction of a magnesium salt and soluble silicate; a salt with basic hydrolysis such as sodium acetate, sodium bicarbonate, sodium phenate, and sodium carbonate; and amine(s), such as a primary, secondary, or tertiary aliphatic amines or aromatic amines, e.g., anilines, n-butyl amine, heterocyclic amines, such as pyridines, piperidines, piperazines, tri-ethyl amine, aliphatic or aromatic diamines and alkanolamines. In particular, amines in the form of their salts with weak organic acids may be used. Conveniently, the basic material is a diamine, such as 2-methylpentamethylenediamine or hexamethylenediamine, which are commercially available from Invista S.à r.l. Corporation under the trade designations DYTEK™ A and DYTEK™ HMD.

Suitable solid basic materials include: basic metal oxide families; alkali on metal oxides; alkaline-earth on metal oxides; alkali and alkaline-earth zeolites; transition metals, rare earth and higher valence oxides; hydrotalcites, calcined hydrotalcites and spinels, specifically hydrotalcites treated with an alkali metal selected from lithium, potassium, sodium, rubidium, cesium, and combinations thereof; perovskites; and beta-aluminas.

In one embodiment, the basic material is one or more of the hindered amines described in U.S. Pat. No. 6,201,157. It will be understood that the basic material may be added in the anhydrous state or may be an aqueous solution of any of the foregoing basic materials, particularly the metal hydroxides and salts with basic hydrolysis.

Conveniently, a liquid basic material employed a neutralization reaction in the present invention, such as an amine or diamine as has been discussed, has a relatively low volatility, with a normal boiling point temperature above that of cyclohexylbenzene, such that it will tend to remain in the bottoms product in subsequent fractionation operations that may be conducted on the least a portion of the treated cleavage reaction product that may contain such liquid basic material.

The conditions at which the neutralization reaction is effected vary with the acid catalyst and basic material employed. Suitable neutralization conditions include a temperature of at least 30° C., or at least 40° C., or at least 50° C., or at least 60° C., or at least 70° C., or at least 80° C., or at least 90° C. Other suitable neutralization conditions include a temperature of no greater than 200° C., or no greater than 190° C., or no greater than 180° C., or no greater than 170° C., or no greater than 160° C., or no greater than 150° C., or no greater than 140° C., or no greater than 130° C., or no greater than 120° C., or no greater than 110° C., or no greater than 100° C. In various embodiments, the neutralization conditions include a temperature that is reduced from cleavage reaction conditions, for example, the temperature may be 1° C., or 5° C., or 10° C., or 15° C., or 20° C., or 30° C., or 40° C. lower than the temperature of the cleavage reaction.

Suitable neutralization conditions may include a pressure of about 1 psig to about 500 psig (5 kPa, gauge to 3450 kPa, gauge), or about 10 psig to 200 psig (70 kPa, gauge to 1380 kPa, gauge) such that the treated cleavage reaction mixture is completely or predominantly in the liquid phase during the neutralization reaction.

After neutralization, the neutralized acid product can be removed from the cleavage product leaving a crude mixture of phenol and cyclohexanone which is then treated to convert at least part of the cyclohexanone to additional phenol.

Cyclohexanone Dehydrogenation

In order to maximize the production of phenol from the benzene starting material, at least part of the cyclohexanone in the cleavage effluent is subjected to dehydrogenation according to the following reaction:

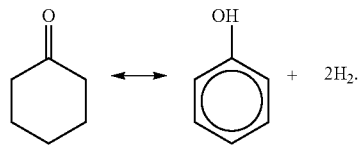

As stated above, cyclohexanone and phenol produce an azeotropic mixture composed of 28 wt % cyclohexanone and 72 wt % phenol, so that any attempt to separate the effluent from the cyclohexylbenzene hydroperoxide cleavage step by simple distillation results in this azeotropic mixture. Moreover, although the efficiency of the separation can be enhanced by conducting the distillation under at least partial vacuum, phenol/cyclohexanone separation remains a costly process. Thus, in one embodiment, the feed to the dehydrogenation step has the same composition as the cleavage effluent, thereby avoiding the need for an initial expensive separation step. Depending on the efficiency of the cyclohexanone dehydrogenation, the final product may contain substantially all phenol, thereby at least reducing the problem of separating the phenol from the cleavage effluent.

In another embodiment, the cleavage effluent is subjected to one or more separation processes to recover or remove one or more components of the effluent prior to dehydrogenation. In particular, the cleavage effluent is conveniently subjected to at least a first separation step to recover some or all of the phenol from the effluent, typically so that the effluent stream fed to said dehydrogenation reaction contains less than 50 wt %, for example less than 30 wt %, such as less than 1 wt %, phenol. The separation of phenol is conveniently effected by vacuum and/or extractive distillation. Additional distillation steps can be used to remove components boiling below 155° C. (as measured at 101 kPa), such as benzene and cyclohexene, and/or components boiling above 185° C. (as measured at 101 kPa), such as 2-phenyl phenol and diphenyl ether, prior to feeding the effluent stream to the dehydrogenation reaction.

The catalyst employed in the cyclohexanone dehydrogenation reaction comprises (i) a support; (ii) a dehydrogenation component comprising at least one metal or compound thereof selected from Groups 6 to 10 of the Periodic Table of Elements; and (iii) tin or a tin compound.

The tin or tin compound may be present in an amount of greater than about 0.01 wt % to about 0.25 wt %, or about 0.02 wt % to about 0.25 wt %, or about 0.03 wt % to about 0.25 wt %, or about 0.04 wt % to about 0.20 wt %, or about 0.05 wt % to about 0.20 wt %, or about 0.05 wt % to about 0.15 wt %, 0.07 wt % to about 0.1 wt % of tin based upon the total weight of the catalyst composition, with ranges from any lower limit to any upper limit being contemplated. In other embodiments, the tin or tin compound may be replaced by another metal component selected from Group 14 of the Periodic Table of Elements.

In various embodiments, the catalyst composition comprises less than 2 wt % of nickel, or <1 wt % nickel, or <0.5 wt % nickel, or less than 0.1 wt % nickel, or no nickel. In various embodiments, the catalyst composition comprises less than 2 wt % of cobalt, or <1 wt % cobalt, or <0.5 wt % cobalt, or less than 0.1 wt % cobalt, or no cobalt. In various embodiments, the catalyst composition is free or substantially free of ruthenium, rhodium, lead and/or germanium, and/or any other active elemental components.

In various embodiments, the ratio of the dehydrogenation component to the tin component (e.g., the Pt/Sn ratio) in the catalyst is greater than 0.5, or greater than 1, or greater than 1.5, or greater than 2.5, or greater than 2.7, or greater than 3, with a ratio of greater than 2.5 to 400, or 2.7 to 200, or 3 to 100 being preferred.

It will be understood that the tin in the catalyst composition may not be purely the elemental metal, but could, for example, be at least partly in another form, such as a salt, oxide, chloride, hydride, sulfide, carbonate, etc. For purposes of this application, the wt % of tin or tin compound in the catalyst composition is calculated based upon the amount of tin used to form the catalyst composition. For purposes of illustration, a catalyst composition made with 1.9 grams of tin chloride salt (1 gram of tin) and 22.29 grams of tetraammine platinum hydroxide solution (4.486 wt % Pt) that is supported on 98 grams of silicon dioxide contains 1 wt % of tin and 1 wt % Pt, based upon total weight of the catalyst composition.

Moreover, for purposes of determining wt % s of various components, only that portion of the support that supports the dehydrogenation component and/or the tin or tin compound shall be considered.

The catalyst support is typically formed of silica, a silicate, an aluminosilicate, carbon (e.g., carbon nanotubes). In one embodiment, the support comprises a crystalline, mesoporous silicate material selected from MCM-41, MCM-48 and MCM-50. In other embodiments, the silica support has a surface area as measured by ASTM D3663 in the range from about 10 $m^2$/gram to about 1000 $m^2$/gram, such as from about 20 $m^2$/gram, to about 500 $m^2$/gram, a pore volume in the range of from about 0.2 cc/gram to about 3.0 cc/gram and a median pore diameter in the range from about 10 angstroms to about 2000 angstroms, such as from about 20 angstroms to about 500 angstrom. Such pore volume and median pore diameter values are determined by mercury intrusion porosimetry as described in ASTM D4284. The support may or may not comprise a binder. Suitable silica supports are described in, for example, PCT Pub. No. WO/2007084440 A1 filed on Jan. 12, 2007 and entitled "Silica Carriers" and is hereby incorporated by reference for this purpose.

Generally, the dehydrogenation component comprises at least one metal component selected from Groups 6 to 10 of the Periodic Table of Elements, such as platinum (Pt) and/or palladium (Pd). Typically, the dehydrogenation component is present in an amount between about 0.1 wt % and about 10 wt % of the catalyst. In one embodiment, the dehydrogenation component is present in an amount between about 0.1 wt % and about 5 wt % of the catalyst or between about 0.2 wt % and about 4 wt % of the catalyst or between about 0.3 wt % and about 3 wt % of the catalyst or between about 0.4 wt % and 2 wt % of the catalyst.

In one embodiment, the catalyst further contains an inorganic base component comprising a metal component selected from an alkali metal, an alkaline earth metal, an alkali metal compound, and an alkaline earth metal compound, especially potassium or a potassium compound. Typically, the inorganic base component is present in an amount between about 0.1 wt % and about 5 wt %, such as between about 0.1 wt % and about 3 wt %, for example between about 0.1 wt % and about 2 wt %, of the catalyst.

The dehydrogenation catalyst is typically prepared by sequentially or simultaneously treating the support, such as by impregnation, with one or more liquid compositions comprising the dehydrogenation component or a precursor thereof, the tin component or a precursor thereof and/or the optional inorganic base component or a precursor in a liquid carrier, such as water. An organic dispersant may be added to each liquid carrier to assist in uniform application of the metal component(s) to the support. Suitable organic dispersants include amino alcohols and amino acids, such as arginine. Generally, the organic dispersant is present in the liquid composition in an amount between about 1 wt % and about 20 wt % of the liquid composition.

In one preferred embodiment, the catalyst is prepared by sequential impregnation with the tin component being applied to the support before the dehydrogenation component.

After treatment with the liquid composition, the support is heated in one or more stages, generally at a temperature of about 100° C. to about 700° C. for a time of about 0.5 to about 50 hours, to effect one or more of (a) removal of the liquid carrier; (b) conversion of a metal component to a catalytically active form; and (c) decompose the organic dispersant. The heating may be conducted in an oxidizing atmosphere, such as air, or under reducing atmosphere conditions, such as hydrogen. After treatment with a liquid composition containing the dehydrogenation component, the support is generally heated at a temperature of about 200° C. to about 500° C., such as about 300° C. to about 450° C., for a time of about 1 to about 10 hours.

In one embodiment, the dehydrogenation catalyst has an oxygen chemisorption value of greater than about 30%, such as greater than about 40%, for example greater than about 50%, even greater than about 60%, greater than about 70%, or even greater than about 80%. As used herein, the oxygen chemisorption value of a particular catalyst is a measure of metal dispersion on the catalyst and is defined as [the ratio of the number of moles of atomic oxygen sorbed by the catalyst to the number of moles of dehydrogenation metal contained by the catalyst]*100%. The oxygen chemisorption values referred to herein are measured using the following technique. Oxygen chemisorption measurements are obtained using the Micromeritics ASAP 2010. Approximately 0.3 to 0.5 grams of catalyst are placed in the Micrometrics device. Under flowing helium, the catalyst is ramped from ambient (i.e., 18° C.) to 250° C. at a rate of 10° C. per minute and held for 5 minutes. After 5 minutes, the sample is placed under vacuum at 250° C. for 30 minutes. After 30 minutes of vacuum, the sample is cooled to 35° C. at 20° C. per minute and held for 5 minutes. The oxygen and hydrogen isotherm is collected in increments at 35° C. between 0.50 and 760 mm Hg. Extrapolation of the linear portion of this curve to zero pressure gives the total (i.e., combined) adsorption uptake.

Suitable conditions for the dehydrogenation step comprise a temperature of about 250° C. to about 500° C. and/or a pressure of about 0.01 atm to about 20 atm (1 kPa to 2000 kPa), such as a temperature of about 300° C. to about 450° C. and a pressure of about 1 atm to about 3 atm (100 kPa to 300 kPa). To improve catalyst stability and assist in extracting the hydrogen generated in the dehydrogenation reaction, hydrogen may be co-fed to the dehydrogenation reaction, typically such that the molar ratio of hydrogen to cyclohexanone in the dehydrogenation feed is about 0:1 to about 4:1.

The reactor configuration used for the dehydrogenation process generally comprises one or more fixed bed reactors containing the dehydrogenation catalyst. Provision can be made for the endothermic heat of reaction, preferably by multiple adiabatic beds with interstage heat exchangers. The temperature of the reaction stream drops across each catalyst bed, and then is raised by the heat exchangers. Preferably, 3 to 5 beds are used, with a temperature drop of about 30° C. to about 100° C. across each bed. Preferably the last bed in the series runs at a higher exit temperature than the first bed in the series.

The effluent from the cyclohexanone dehydrogenation reaction is composed mainly of phenol and hydrogen. The desired phenol is easily removed from the reaction effluent by fractionation to leave a hydrogen stream which, after suitable purification, can be recycled to the benzene hydroalkylation step.

By employing the present dehydrogenation process, substantially all the cyclohexanone in the cyclohexylbenzene hydroperoxide cleavage effluent can be converted to phenol. In practice, however, depending on market conditions, there is likely to be a significant demand for cyclohexanone product. This can readily met using the present process by reliance on the reversible nature of the reaction (2), namely by hydrogenating at least some of the phenol back to cyclohexanone. This can readily be achieved by, for example, contacting the phenol with hydrogen in the presence of a hydrogenation catalyst, such as platinum or palladium, under conditions including a temperature of about 20° C. to about 250° C., a pressure of about 101 kPa to about 10000 kPa and a hydrogen to phenol molar ratio of about 1:1 to about 100:1.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam and nylons, such as nylon 6 and nylon 6,6.

The phenol produced through the processes disclosed herein may be used, for example, to produce phenolic resins, bisphenol A, ε-caprolactam, adipic acid and/or plasticizers.

The invention will now be more particularly described with reference to the following non-limiting Examples and the accompanying drawings.

Example 1 (Comparative)

Production of Catalyst Comprising 1% Pt, 0.50% K on a Silica Support

A 1/20 inch (0.13 cm) silica extrudate was impregnated with 0.50 wt % K as potassium carbonate using incipient wetness impregnation and dried at 121° C. After drying the 0.50 wt % potassium containing silica extrudate was calcined in air at 538° C. The calcined 0.50% K containing silica extrudate was then impregnated with 1% Pt as tetraammine platinum hydroxide using incipient wetness impregnation and dried at 121° C. After drying the 1% Pt, 0.50% K containing silica extrudate was calcined in air at 350° C.

Example 2

Production of 0.1% Sn/1% Pt//SiO$_2$ Catalyst

A catalyst was prepared by initially impregnating a silica extrudate with an aqueous solution of tetraammine Pt nitrate. After drying in air at 121° C., the resultant platinum-containing extrudate was impregnated with an aqueous solution of tin chloride and then dried in air at 121° C. Part of the resultant product was retained (uncalcined catalyst 2A) and part was calcined in air at 350° C. for 3 hours before being used in subsequent catalyst testing (calcined catalyst 2B). The compositions of the catalysts are summarized in Table 1.

Examples 3 to 8

Production of 1% Pt/x % Sn/SiO$_2$ Catalysts

Five additional catalysts containing 1 wt % platinum and varying amounts of tin, namely 0.05 wt % (Example 3), 0.1 wt % (Example 4), 0.15 wt % (Example 5), 0.25 wt % (Example 6), 0.5 wt % (Example 7), and 1 wt % (Example 8), were prepared by incipient wetness impregnation. In each case, a 1/20 inch quadrulobe silica extrudate was initially impregnated with an aqueous solution of tin chloride and then dried in air at 121° C. The resultant tin-containing extrudates were then impregnated with an aqueous solution of tetraammine Pt nitrate and again dried in air at 121° C. Each of resultant products was calcined in air at 350° C. for 3 hours before being used in subsequent catalyst testing. The compositions of the catalysts are summarized in Table 1.

Example 9

Production of 1% Pt/1% Sn/0.5% K/SiO$_2$Catalyst

A potassium, tin and platinum containing 1/20" quadrulobe silica extrudates was prepared by incipient wetness impregnation. Initially, the silica extrudate was impregnated with an aqueous solution of potassium carbonate, then dried in air at 121° C. and calcined again in air at 538° C. for 3 hours. The potassium-containing extrudate was then impregnated with an aqueous solution of tin chloride and then dried in air at 121° C. The resultant potassium and tin-containing extrudate was then impregnated with an aqueous solution of tetraammine Pt nitrate and again dried in air at 121° C. Each of resultant products was divided into two parts; a first part, designated A, which was used without calcination in subsequent catalyst testing and a second part, designated B, which was calcined in air at 350° C. for 3 hours before being used in subsequent catalyst testing. The compositions of the catalysts are summarized in Table 1.

Example 10

Chemisorption Testing

The hydrogen and oxygen chemisorption of each of the calcined and uncalcined samples of Examples 1 to 9 was measured on a Micromeritics ASAP2010 instrument using the following chemisorpton procedure.

| Task | Step | Gas | Temp (° C.) | Rate (° C./min) | Time (min) |
|---|---|---|---|---|---|
| 1 | Flow | Helium | 200 | 10 | 30 |
| 2 | Flow | Hydrogen | 250 | 10 | 30 |
| 3 | Flow | Helium | 250 | 10 | 5 |
| 4 | Evacuation |  | 250 | 0 | 60 |
| 5 | Evacuation |  | 35 | 20 | 5 |
| 6 | Leak Test |  | 35 | 0 |  |
| 7 | Isotherm | Hydrogen or Oxygen | 35 | 0 |  |

The chemisorption results are summarized in Table 1.

Example 11

Benzene Hydrogenation Testing

Certain of the catalysts of Examples 1 to 9 were further characterized by measuring their benzene hydrogenation activity (1$^{st}$ order rate constant at 100° C.) using the following procedure.
1. Purge—Start helium flow at 200 sccm, purge time 5 mins.
2. Drying—Ramp to 110° C. at 5° C./min, hold time for 60 mins.
3. Reduction—reduce at 350° C. (for Pd) 250° C. (for Pt), H$_2$ flow at 200 sccm, hold time of 1 hr.
4. Reaction temperature range is 50° C., 75° C., 100° C., 125° C., 1$^{st}$ order rate constant at 100° C. is reported as the BHA No. in Table 1.

TABLE 1

| Example | Pt, wt % | Sn, wt % | K, wt % | H$_2$ Dispersion | O$_2$ Dispersion | BHA |
|---|---|---|---|---|---|---|
| 2A | 1 | 0.10 | 0 | 24% | 26% | 330 |
| 2B | 1 | 0.10 | 0 | 35% | 29% | 170 |
| 3 | 1 | 0.05 | 0 | 54% | 36% | 200 |
| 4 | 1 | 0.10 | 0 | 34% | 25% | 150 |
| 5 | 1 | 0.15 | 0 | 9% | 29% | 85 |
| 6 | 1 | 0.25 | 0 | 5% | 21% | 21 |
| 7 | 1 | 0.5 | 0 | 4% | 20% | 16 |
| 8 | 1 | 1 | 0 | 1% | 16% | 2 |
| 9A | 1 | 1 | 0.5 | 1% | 16% | 21 |
| 9B | 1 | 1 | 0.5 | 1% | 6% | 2 |

Example 12

Cyclohexanone (CHO) Dehydrogenation Testing

The reactor used in these experiments consisted of a 316 stainless steel tube with dimensions of 22 inches (56 cm) long, 0.5 inch (1.3 cm) outside diameter and 0.035 inch (0.09 cm) wall thickness. A piece of 316 stainless steel tubing 8.75 inches (22 cm) long and 0.375 inch (0.95 cm) outside diameter and a piece of 0.25 inch (0.64 cm) tubing of similar length was used in the bottom of the reactor as a spacer (one inside of the other) to position and support the catalyst in a isothermal zone of a furnace. A 0.25 inch (0.64 cm) plug of glass wool was placed at the top of the spacer to keep the catalyst in place. A 0.125 inch (0.32 cm) stainless steel thermo-well was placed in the catalyst bed, the thermo-well being long enough to monitor temperature throughout the catalyst bed using a movable thermocouple.

Each catalyst sample was pressed into pellets then crushed and sized to 20-40 US sieve mesh. Typically 5.0 grams, volume 12.5 cc, of the catalyst was presized to 20-40 mesh and used as a standard loading. The catalyst was then loaded into the reactor from the top. The catalyst bed typically was 15 cm in length. A 0.25 inch (0.64 cm) plug of glass wool was placed at the top of the catalyst bed to separate quartz chips from the catalyst. The remaining void space at the top of the reactor was filled with quartz chips. The reactor was installed in the furnace with the catalyst bed in the middle of the furnace at a pre-marked isothermal zone. The reactor was then pressure and leak tested typically at 300 psig (2170 kPa).

Each catalyst sample was pre-conditioned in situ by heating to 375° C. to 460° C. with H$_2$ flow at 100 cc/min and held for 2 hours. A 500 cc ISCO syringe pump was used to introduce the cyclohexanone to the reactor. The feed was pumped through a vaporizer before flowing through heated lines to the reactor. A Brooks mass flow controller was used to set the hydrogen flow rate. A Grove "Mity Mite" back pressure controller was used to control the reactor pressure typically at 100 psig (790 kPa). GC analyses were taken to verify feed composition. The feed was then pumped through the catalyst bed held at the reaction temperature of 375° C. to 460° C., preferably at 460° C., at a WHSV of 2-15 and a pressure of 100 psig (790 kPa). The products exiting the reactor flowed through heated lines routed to two collection pots in series. The non-condensable gas products routed to an on line HP 5890 GC. The first pot was heated to 60° C. and the second pot cooled with chilled coolant to about 10° C. Material balances were taken at 12 to 24 hrs intervals. Samples were taken and diluted with 50% ethanol for analysis. A Hewlett Packard 6890 gas chromatograph with FID detector and with an Agilent technologies GC column 30 m×0.32 mm×0.25 micron film thickness was used for the analyses of the hydrocarbon products. Non-condensable gas products analyses were taken on line via a HP 5980 Gas Chromatograph with J and W Scientific column 60 m×0.25 mm ID×1.0 micron film. The HP 6890GC analysis ramp program was set to: 40° C. for 0 min; 5° C./min to 150° C., held 0 min; 10° C./min to 260° C. held 28 min; total analysis time was 60 min; and the HP 5890 GC ramp was set to: −30° C. for 5 min, 5° C./min to 80° C. for 2 min, 5° C./min to 200° C. for 0 min, 15° C./min to 240° C. held to the end total analysis time of 60 min.

The results of the cyclohexanone testing of the catalysts of Examples 1 to 9 are summarized in the accompanying drawings.

Figure 2:
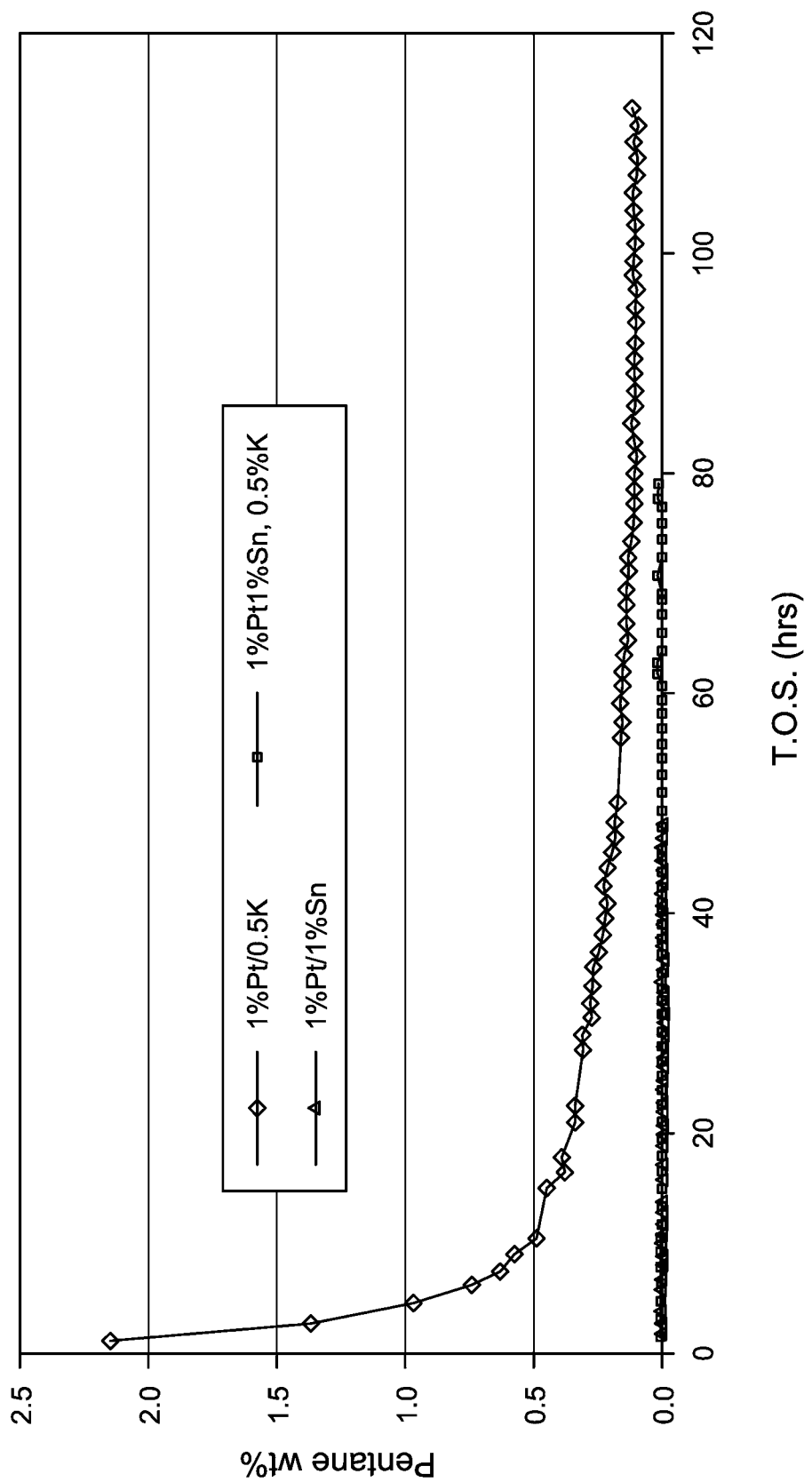
FIG. 2 is a graph comparing pentane production against time on stream for the 1% Pt/1% Sn/$SiO_2$ catalyst of Example 7 and the 1% Pt/1% Sn/0.5% K/$SiO_2$ catalyst of Example 9B with that of the 1% Pt/0.5% K/$SiO_2$ catalyst of Comparative Example 1.
Figure 3:
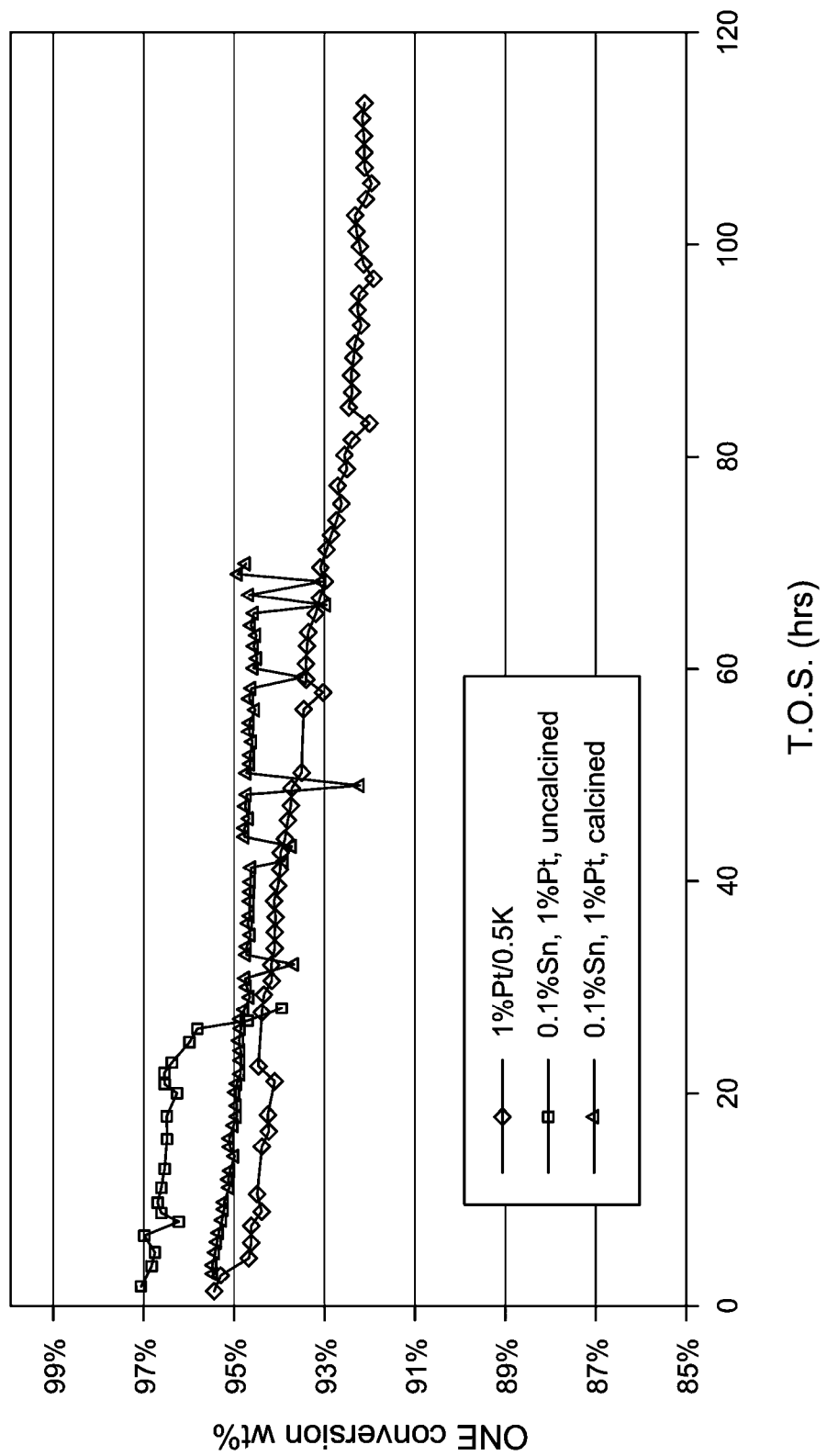
FIG. 3 is a graph comparing cyclohexanone conversion against time on stream for the uncalcined and calcined 0.1% Sn/1% Pt/$SiO_2$ catalysts of Examples 2A and 2B with that of the 1% Pt/0.5% K/$SiO_2$ catalyst of Comparative Example 1.
Figure 4:
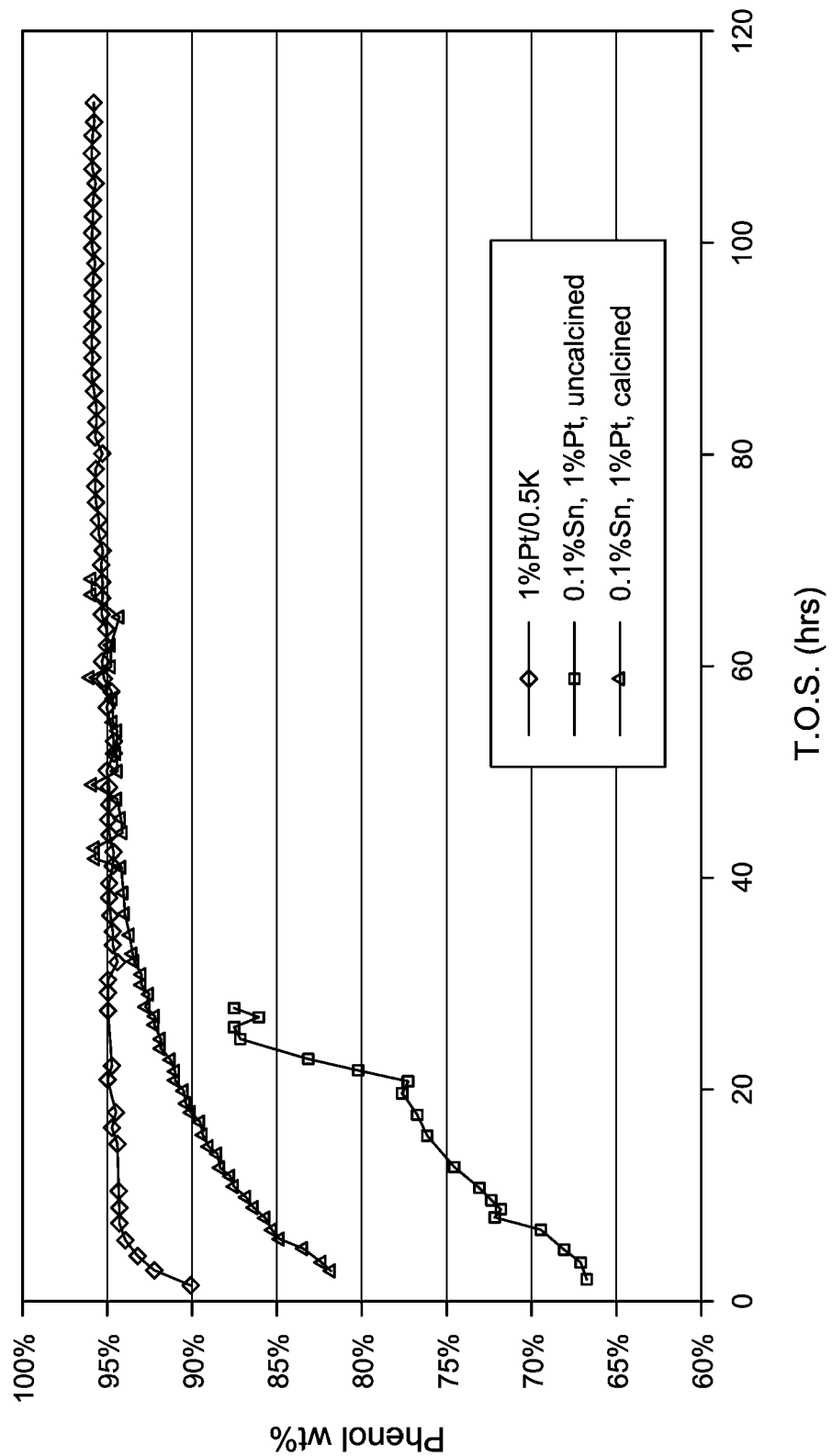
FIG. 4 is a graph comparing phenol production against time on stream for the uncalcined and calcined 0.1% Sn/1% Pt/$SiO_2$ catalysts of Examples 2A and 2B with that of the 1% Pt/0.5% K/$SiO_2$ catalyst of Comparative Example 1.
Figure 5:
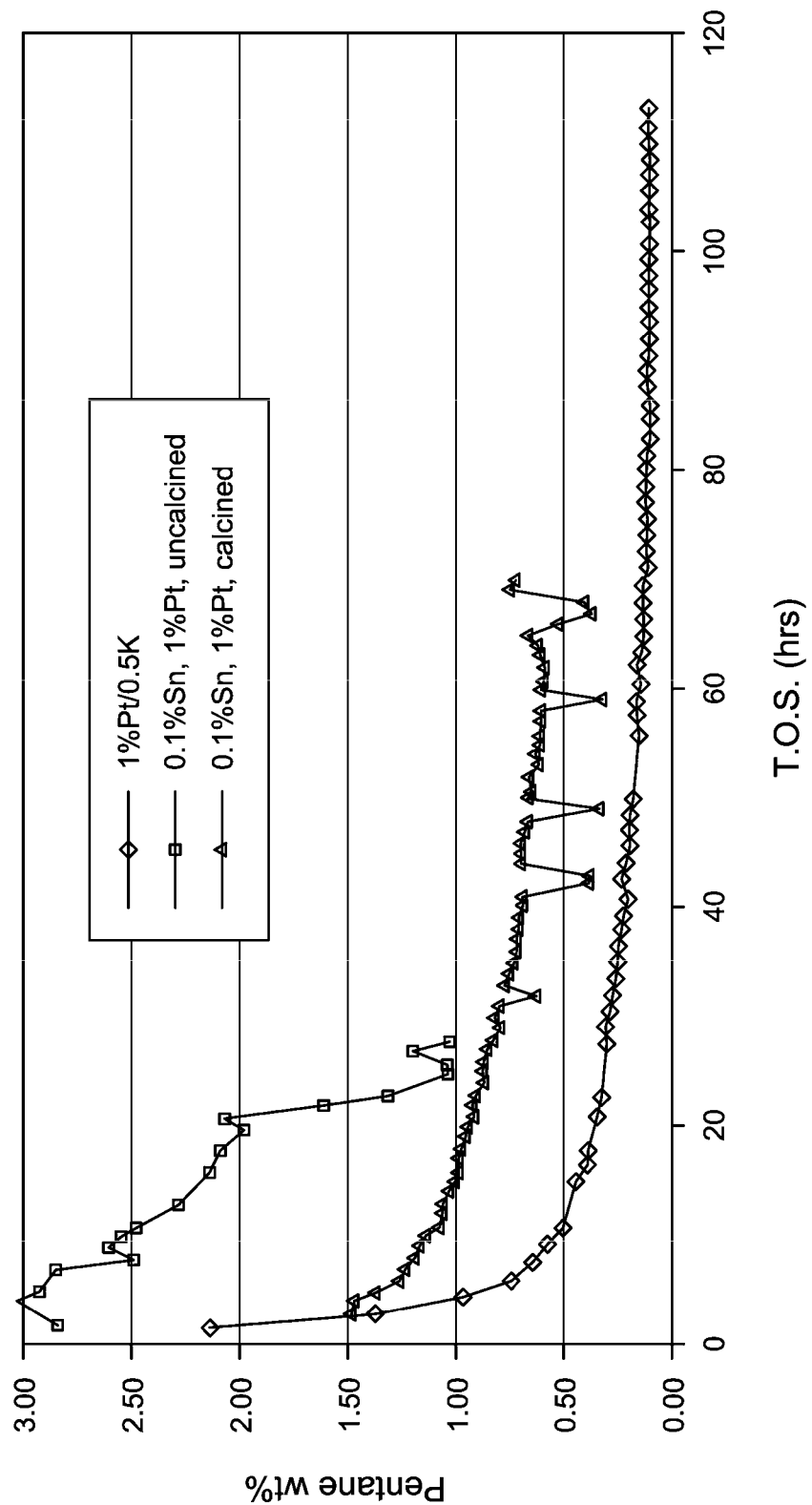
FIG. 5 is a graph comparing pentane production against time on stream for the uncalcined and calcined 0.1% Sn/1% Pt/$SiO_2$ catalysts of Examples 2A and 2B with that of the 1% Pt/0.5% K/$SiO_2$ catalyst of Comparative Example 1.

FIG. 1 show that presence of Sn at 1 wt % in a calcined 1 wt % Pt/SiO$_2$ catalyst, both with and without the presence of 0.5 wt % K (Examples 9B and 8, respectively) resulted in lower catalyst activity and higher catalyst deactivation compared to the catalyst of Comparative Example 1 without Sn. This is illustrated with reference to conversion of cyclohexanone (CHO). However, a dramatic decrease in the pentane formation was observed (FIG. 2). When 0.10 wt % Sn was added to the Pt/support without and with calcination, Examples 2A and 2B, the data show that this approach improves the catalyst activity and higher cyclohexanone conversion was obtained. The calcined sample of Example 2B shows better stability than the non-calcined sample of Example 2A and the K/Pt catalyst of Comparative Example 1 (FIG. 3). The calcined sample of Example 2B also shows better selectivity to phenol than the non-calcined sample of Example 2A (FIG. 4), but its pentane selectivity is higher than the Pt/K catalyst of Comparative Example 1 (FIG. 5).

Figure 6:
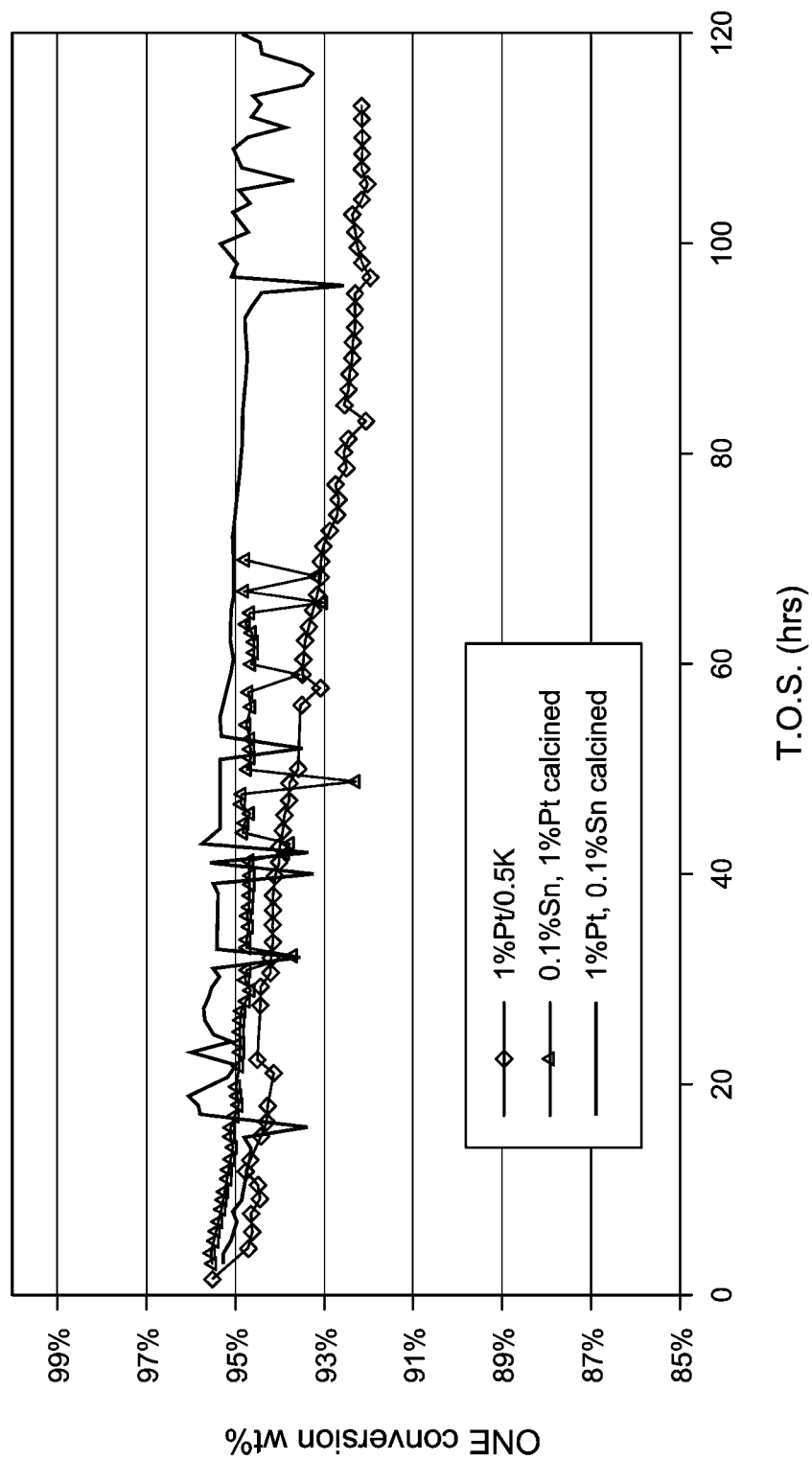
FIG. 6 is a graph comparing cyclohexanone conversion against time on stream for the calcined 1% Pt/0.1% Sn/$SiO_2$ catalyst of Example 4 with that of the calcined 0.1% Sn/1% Pt/$SiO_2$ catalyst of Example 2B and that of the calcined 1% Pt/0.5% K/$SiO_2$ catalyst of Comparative Example 1.
Figure 7:
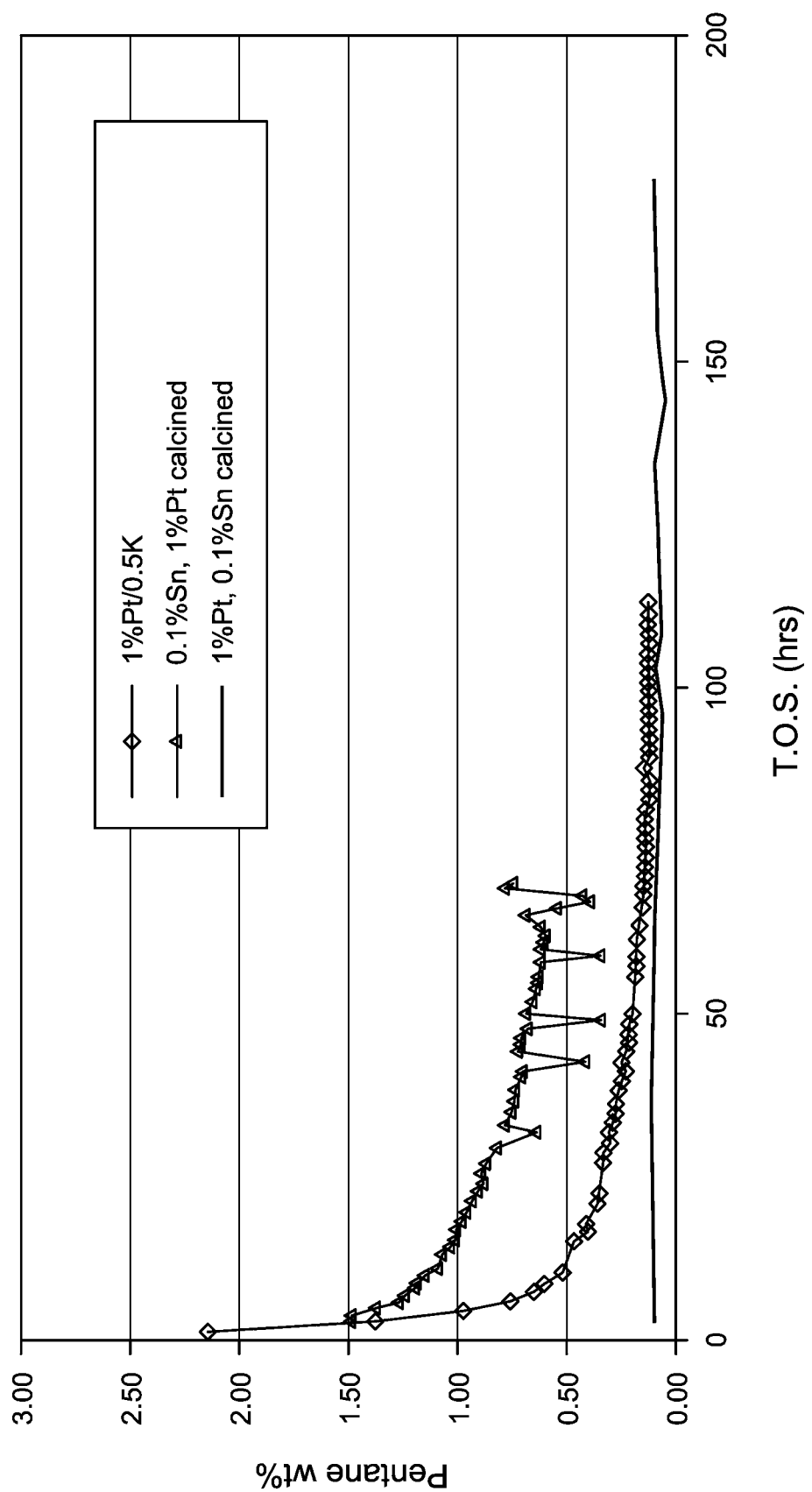
FIG. 7 is a graph comparing pentane production against time on stream for the calcined 1% Pt/0.1% Sn/$SiO_2$ catalyst of Example 4 with that of the calcined 0.1% Sn/1% Pt/$SiO_2$ catalyst of Example 2B and that of the calcined 1% Pt/0.5% K/$SiO_2$ catalyst of Comparative Example 1.
Figure 8:
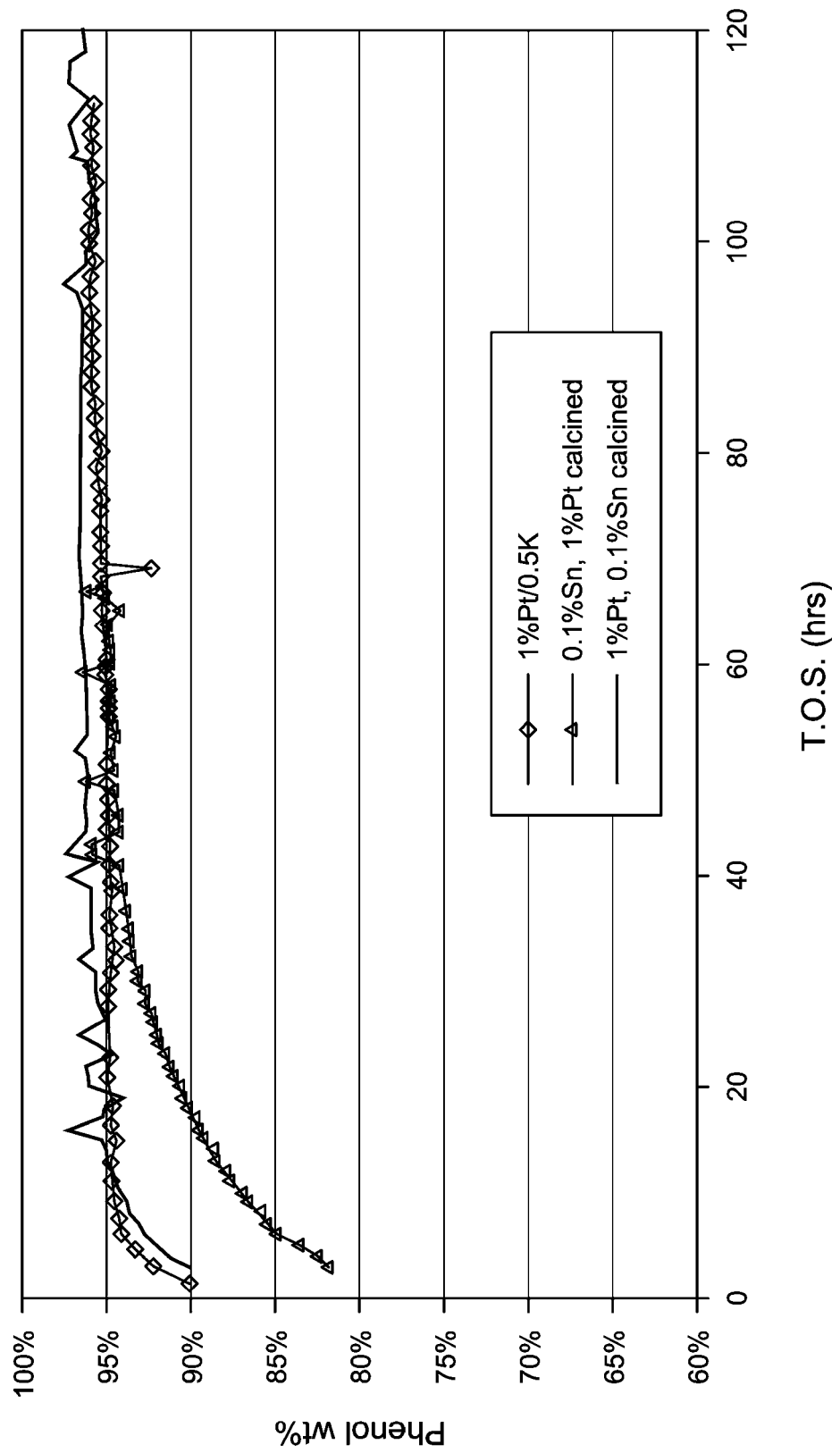
FIG. 8 is a graph comparing phenol production against time on stream for the calcined 1% Pt/0.1% Sn/$SiO_2$ catalyst of Example 4 with that of the calcined 0.1% Sn/1% Pt/$SiO_2$ catalyst of Example 2B and that of the calcined 1% Pt/0.5% K/$SiO_2$ catalyst of Comparative Example 1.

The data show that the addition sequence of the Pt and Sn did not affect the catalyst activity and stability, both catalysts showing similar cyclohexanone conversion and similar catalyst deactivation. Thus, the calcined 0.1% Sn/1% Pt/SiO$_2$ catalyst of Example 2B and the calcined 1% Pt/0.1% Sn/SiO$_2$ catalyst of Example 8 show similar improvement in the catalyst activity and stability as compared with the Pt/K catalyst of Comparative Example 1 (FIG. 6). Unexpectedly, however, the Sn addition sequence dramatically affects the pentane formation. Thus, as shown in FIG. 7, when the Sn was added first then the Pt as in Example 8, the catalyst showed reduced pentane production and pentylbenzene was below GC detection limit as compared to the catalyst of Example 2B, where Pt was added to the support first then the Sn. Similarly, FIG. 8 shows that better selectivity to phenol was observed with the catalyst of Example 8 (Sn added first) as compared to the catalyst of Example 2B (Pt added first).

Figure 9:
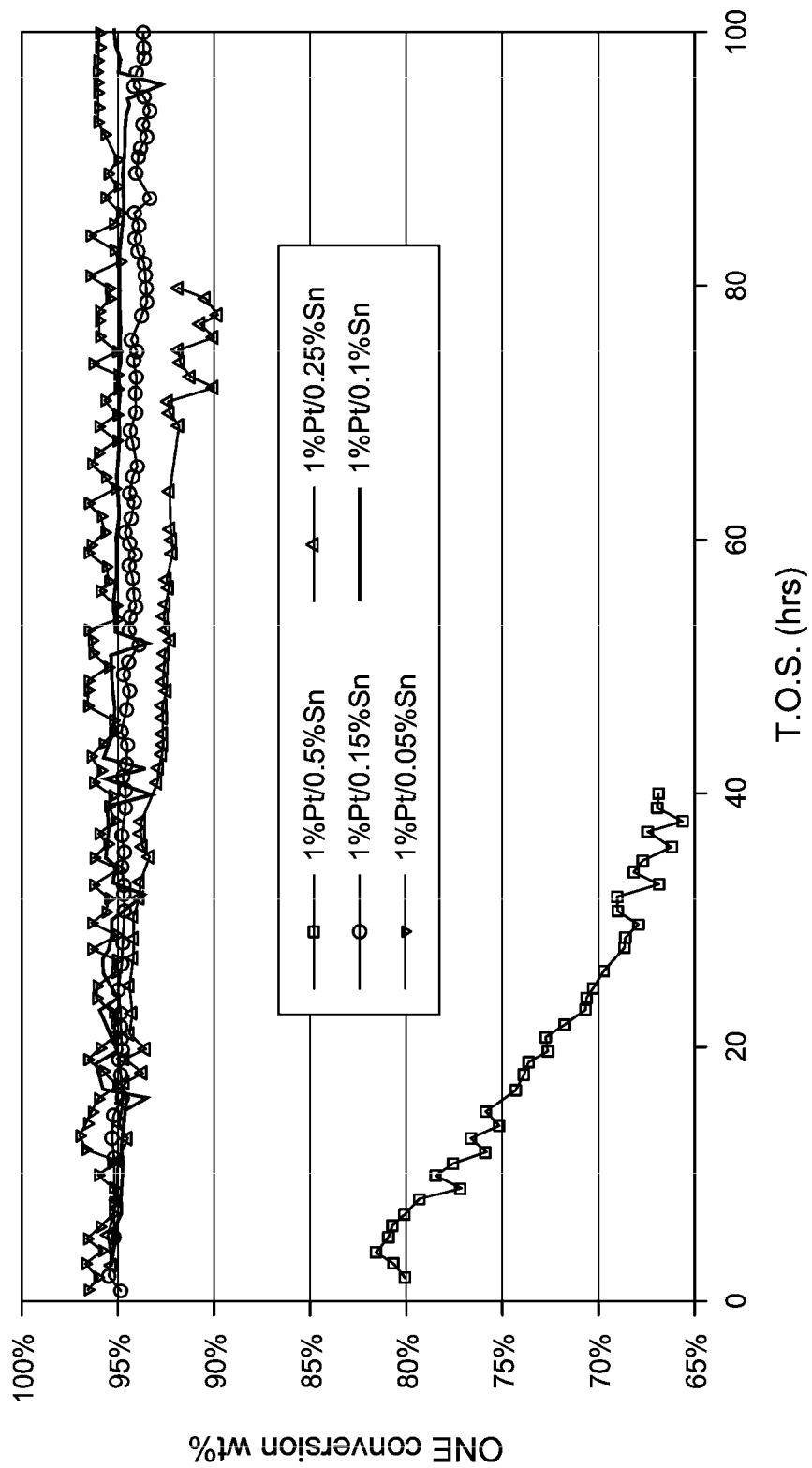
FIG. 9 is a graph comparing cyclohexanone conversion against time on stream for the calcined 1% Pt/x % Sn/$SiO_2$ catalysts of Examples 3 to 8.

FIG. 9 demonstrates the addition of Sn in amounts in excess of 0.15 wt % has a deleterious effect on catalyst stability and activity. Both 0.05 wt % and 0.1 wt % Sn catalyst showed similar catalyst deactivation.

Figure 10:
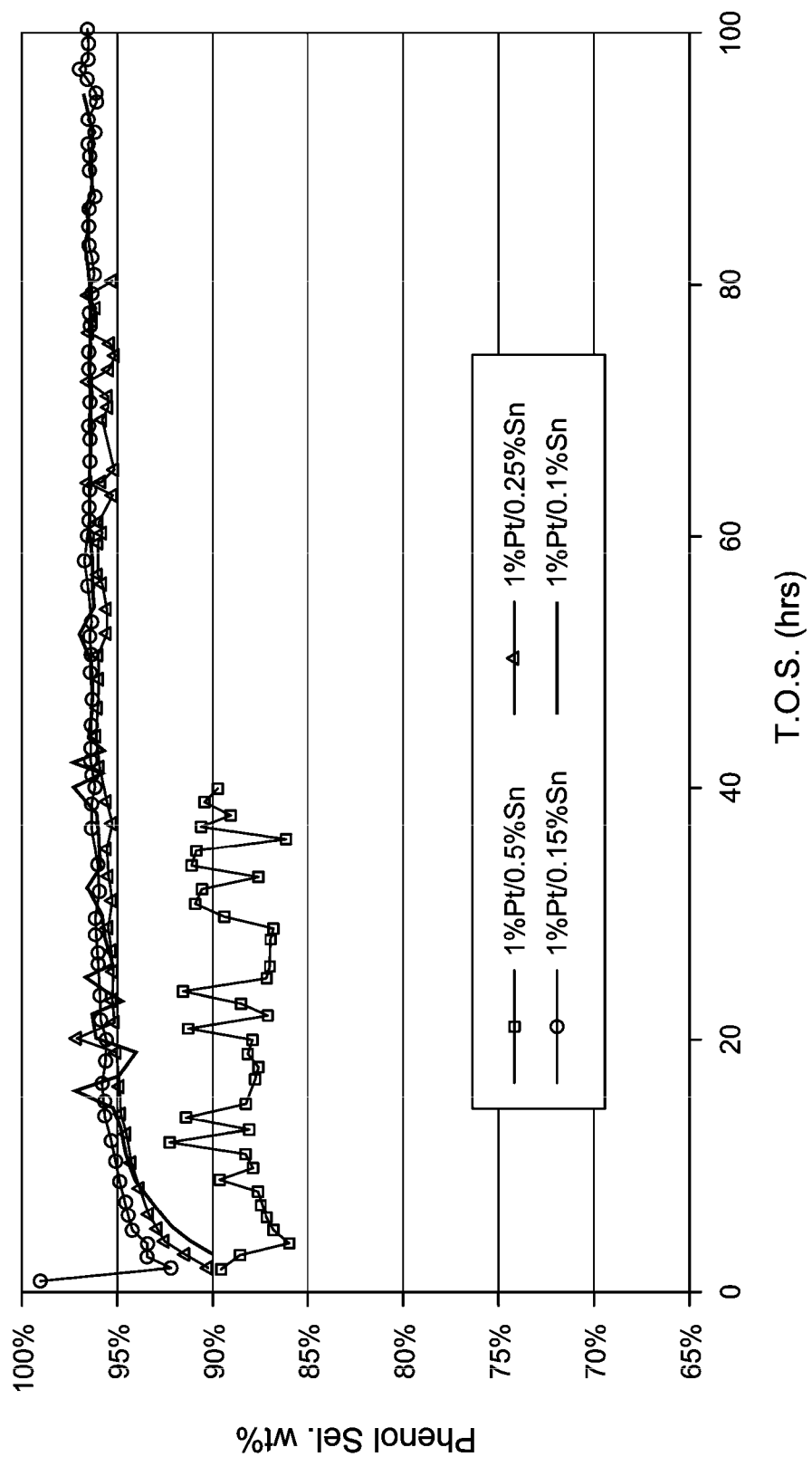
FIG. 10 is a graph comparing phenol production against time on stream for the calcined 1% Pt/x % Sn/$SiO_2$ catalysts of Examples 3 to 8.
Figure 11:
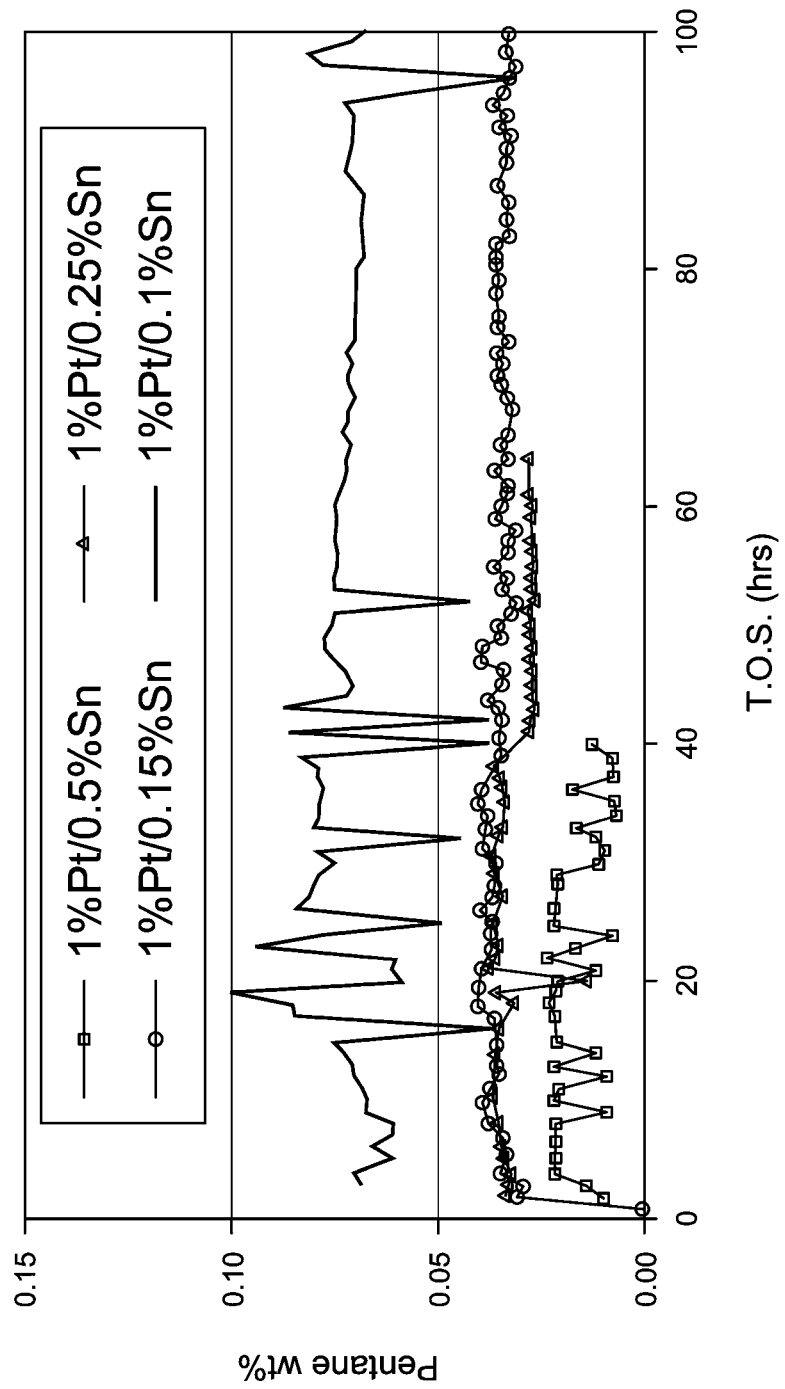
FIG. 11 is a graph comparing pentane production against time on stream for the calcined 1% Pt/x % Sn/$SiO_2$ catalysts of Examples 3 to 8.

FIG. 10 demonstrates that catalysts which contain <0.25 wt % Sn show similar phenol selectivity, whereas FIG. 11 demonstrates that increasing the Sn content lowers the selectivity of the catalyst to pentane formation. The pentylbenzene selectivity was consistently below the GC detection limit.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for the dehydrogenation of a ketone to an aromatic alcohol, the process comprising contacting a feed comprising a cycloaliphatic alcohol or ketone under dehydrogenation conditions with catalyst composition comprising: (i) a support; (ii) a dehydrogenation component comprising at least one metal or compound thereof selected from Groups 6 to 10 of the Periodic Table of Elements; and (iii) tin or a tin compound, wherein the tin is present in an amount of 0.01 wt % to about 0.25 wt %, the wt % based upon the total weight of the catalyst composition; and further wherein said dehydrogenation conditions comprise a temperature of about 250° C. to about 500° C., a pressure of about 100 kPa to about 3550 kPa, a weight hourly space velocity of about 0.2 hr$^{-1}$ to 50 hr$^{-1}$, and a hydrogen to cyclohexanone-containing feed molar ratio of about 2 to about 20.

2. The process of claim 1, wherein said feed comprises cyclohexanone.

3. The process of claim 1, wherein said at least one metal selected from Groups 6 to 10 of the Periodic Table of Elements comprises platinum, palladium and mixtures thereof.

4. A process for producing phenol from benzene, the process comprising:
    (a) reacting benzene and hydrogen with a catalyst under hydroalkylation conditions to produce cyclohexylbenzene;
    (b) oxidizing cyclohexylbenzene from (a) to produce cyclohexylbenzene hydroperoxide;
    (c) converting cyclohexylbenzene hydroperoxide from (b) to produce an effluent steam comprising phenol and cyclohexanone; and
    (d) contacting at least a portion of the effluent stream from (c) with a dehydrogenation catalyst comprising: (i) a support; (ii) a dehydrogenation component comprising at least one metal or compound thereof selected from Groups 6 to 10 of the Periodic Table of Elements; and (iii) tin or a tin compound, wherein the tin is present in an amount of 0.01 wt % to about 0.25 wt %, the wt % based upon the total weight of the catalyst composition, wherein the contacting occurs under dehydrogenation conditions effective to convert at least part of the cyclohexanone in the effluent stream into phenol and hydrogen; and further wherein said dehydrogenation conditions comprise a temperature of about 250° C. to about 500° C., a pressure of about 100 kPa to about 3550 kPa, a weight hourly space velocity of about 0.2 hr$^{-1}$ to 50 hr$^{-1}$, and a hydrogen to cyclohexanone-containing feed molar ratio of about 2 to about 20.

* * * * *